US008448638B2

(12) United States Patent
Chen et al.

(10) Patent No.: US 8,448,638 B2
(45) Date of Patent: May 28, 2013

(54) ANESTHETIC VAPORIZER

(75) Inventors: Donghua Chen, Shenzhen (CN); Daoming Gong, Shenzhen (CN); Wei Wang, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 760 days.

(21) Appl. No.: 12/566,921

(22) Filed: Sep. 25, 2009

(65) Prior Publication Data
US 2010/0242962 A1  Sep. 30, 2010

(30) Foreign Application Priority Data

Sep. 28, 2008 (CN) .......................... 2008 1 0216455

(51) Int. Cl.
*A61M 11/00* (2006.01)
(52) U.S. Cl.
USPC ............ 128/204.13; 128/203.12; 128/203.25; 128/204.14; 128/204.22
(58) Field of Classification Search
USPC ............ 128/204.13, 203.12, 203.14, 203.25, 128/204.14, 204.22
See application file for complete search history.

(56) References Cited

U.S. PATENT DOCUMENTS

| | | | | |
|---|---|---|---|---|
| 3,630,438 A | * | 12/1971 | Bickford | .................. 236/53 |
| 4,436,674 A | * | 3/1984 | McMenamin | ............... 261/64.3 |
| 4,444,182 A | | 4/1984 | Gregory | |
| 4,770,168 A | * | 9/1988 | Rusz et al. | ............... 128/203.12 |
| 5,649,531 A | * | 7/1997 | Heinonen | ................ 128/203.12 |
| 5,671,729 A | | 9/1997 | Moll | |
| 5,832,917 A | * | 11/1998 | Sarela et al. | ............. 128/203.12 |
| 5,918,595 A | * | 7/1999 | Olsson et al. | ............ 128/203.26 |
| 7,836,882 B1 | * | 11/2010 | Rumph et al. | ........... 128/203.12 |
| 2005/0133030 A1 | | 6/2005 | Fiedorowicz | |

FOREIGN PATENT DOCUMENTS

| | | |
|---|---|---|
| CN | 1038938 | 1/1990 |
| CN | 1868551 | 11/2006 |
| JP | 2000005315 | 1/2000 |

OTHER PUBLICATIONS

Chinese Search Report dated Oct. 30, 2008 for Chinese Patent Application No. 200810216455.1.
English Abstract for Chinese Patent Application No. CN 1038938.
English Abstract for Chinese Patent Application No. CN 1868551.
English Abstract for Japanese Patent Application No. JP 2000005315.

* cited by examiner

*Primary Examiner* — Steven Douglas
(74) *Attorney, Agent, or Firm* — Vista IP Law Group, LLP

(57) ABSTRACT

An anesthetic vaporizer is disclosed herein which comprises a fresh gas inlet, a mixed gas outlet, a first gas branch circuit, a second gas branch circuit and a vaporizing chamber. The vaporizing chamber has a reservoir for containing an anesthetic agent. The first gas branch circuit connects the fresh gas inlet and the mixed gas outlet. The second gas branch circuit comprises a first pneumatic circuit, a pressure compensation unit, a second pneumatic circuit, a wick unit and a third pneumatic circuit. The pressure compensation unit has a curved, continuous and sealed vent slot. The wick unit has an immersion portion which is directly contacted with the anesthetic agent in the reservoir. The fresh gas inlet, the first pneumatic circuit, the vent slot, the second pneumatic circuit, the wick unit, the third pneumatic circuit and the mixed gas outlet are sequentially connected with one another. The pressure compensation unit is provided in the reservoir and has a heat conductor which is directly contacted with the anesthetic agent to transfer heat. The vent slot is formed in the heat conductor. The anesthetic vaporizer according to the invention can stabilize the concentration of the anesthetic vapor in the outputted mixed gas.

20 Claims, 5 Drawing Sheets

ANESTHETIC VAPORIZER

CROSS-REFERENCE TO RELATED APPLICATIONS

The present application claims priority to Chinese Patent Application No. 200810216455.1, filed on Sep. 28, 2008, which is hereby incorporated by reference in its entirety.

FIELD OF THE INVENTION

The present invention relates to an anesthetic vaporizer.

BACKGROUND OF THE INVENTION

An anesthetic vaporizer is an apparatus that can be used to effectively vaporize a liquid anesthetic agent, and can precisely input the liquid anesthetic agent at a certain concentration into an anesthesia breathing circuit, which is able to eliminate the influences of changes in temperature and pressure and the like on the concentration output thereof.

As illustrated in FIG. 1, the anesthetic vaporizer typically comprises a fresh gas inlet 1', a pressure compensation unit 2', a fresh gas control valve 3', a wick unit 4', a bypass circuit 5', a temperature compensation unit 6', a concentration control unit 7', a mixed gas outlet 8', a filling unit 9', and a vaporizing chamber 10'. The fresh gas inlet 1', the bypass circuit 5', the temperature compensation unit 6', the concentration control unit 7' and the mixed gas outlet 8' are sequentially connected with one another; while the fresh gas inlet 1', the pressure compensation unit 2', the fresh gas control valve 3', the wick unit 4', the concentration control unit 7' and the mixed gas outlet 8' are sequentially connected with one another. The vaporizing chamber 10' has a reservoir for storing anesthetic agent. A part of the wick unit 4' is immersed into the anesthetic agent. The pressure compensation unit 2' is positioned outside the reservoir of the vaporizing chamber 10'. The reservoir of the vaporizing chamber 10' is through a passage connected to the filling unit 9' for injecting the anesthetic agent into the reservoir.

Fresh gas flows into the vaporizer through the fresh gas inlet 1'. A part of the gas flows into the wick unit 4' through the fresh gas control valve 3' after passing through the pressure compensation unit 2'. A part of the wick unit 4' is immersed into the anesthetic agent so that the wick unit 4' is filled with the saturated vapor of anesthetic gas. When the fresh gas flows through the wick unit 4', the fresh gas will be mixed with parts of the anesthetic vapor. The fresh gas carrying the anesthetic vapor flows into the concentration control unit 7' after passing through the wick unit 4'. The other part of the fresh gas flows into the bypass circuit 5' of the vaporizer, then flows into the concentration control unit 7' after passing through the temperature compensation unit 6', and meets the fresh gas carrying the anesthetic vapor in the concentration control unit 7'. By the controlling of the concentration control unit 7', the two streams of gases are mixed at a certain ratio and outputted out of the vaporizer from the mixed gas outlet 8'.

When the vaporizer is used continuously, the temperature of the vaporizer drops since the anesthetic agent has to absorb heat to vaporize, which in turn reduces the evaporation speed of the anesthetic agent since the evaporation speed of the liquid decreases as the temperature drops. Thus, the concentration of the anesthetic vapor outputted from the vaporizer is reduced accordingly. In order to prevent the concentration of the vaporizer from changing due to temperature dropping, in the vaporizer being subjected to temperature change, the temperature compensation unit 6' will change the vent aperture of its valve opening to increase or decrease the gas flow of the bypass circuit 5', so that the concentration output of the vaporizer does not change according to temperature change. The temperature compensation unit 6' may be implemented as a valve body which may control the gas flow of the bypass circuit 5', the operation principle of which is to take advantage of the difference between the expansion coefficients of different metals to change the size of the temperature compensation valve opening so as to change the vent aperture for the gas.

The pressure compensation unit 21 has two main functions as follows: (1) When the pressure at the mixed gas outlet 8' changes due to mechanical ventilation, it will be prevented by the pressure compensation unit 2' consisting of spiral pipeline that the gas may reversely flow due to pressure change to bring the gas carrying the anesthetic vapor to the fresh gas inlet 1' so as to influence the concentration output; (2) When the pressure at the fresh gas inlet 1' changes, the pressure compensation unit 2' consisting of spiral pipeline will attenuate the change of the gas caused by the pressure change and stabilize the flow speed of the gas.

However, this kind of anesthetic vaporizer typically has the following disadvantages: (1) Although there is a temperature compensation unit, since the temperature compensation unit and the pressure compensation unit are independent to each other, then when in use, the temperature compensation unit is unable to change the temperature of the vaporizer and the pressure compensation unit is unable to serve the function of adjusting temperature, the two units cannot be combined together, resulting in that when in use, the temperature of the vaporizer will gradually drops and accordingly the vaporization speed of the anesthetic agent will slow down and the deviation of the concentration of the anesthetic vapor in the outputted mixed gas from the set concentration will be increased, over time; (2) When being placed outside the vaporizer, the pressure compensation unit occupies the space outside the vaporizer so that the structure of the vaporizer is not compact, and when being placed inside the vaporizer, the pressure compensation unit is required to be assembled together with other units so that the structure and assembly are complicated.

SUMMARY OF THE INVENTION

The technical problem to be solved by the present invention is to overcome the disadvantages in the prior art and to provide an anesthetic vaporizer that can provide a steady output of concentration of the anesthetic vapor in the mixed gas.

The technical solution of the present invention designed to solve the above technical problem is directed to an anesthetic vaporizer comprising a fresh gas inlet, a mixed gas outlet, a first gas branch circuit, a second gas branch circuit and a vaporizing chamber. The vaporizing chamber has a reservoir for containing anesthetic agent. The first gas branch circuit connects the fresh gas inlet and the mixed gas outlet. The second gas branch circuit comprises a first pneumatic circuit, a pressure compensation unit, a second pneumatic circuit, a wick unit and a third pneumatic circuit. The pressure compensation unit has a curved, continuous and sealed vent slot. The wick unit has an immersion portion which is directly contacted with the anesthetic agent in the reservoir. The fresh gas inlet, the first pneumatic circuit, the vent slot, the second pneumatic circuit, the wick unit, the third pneumatic circuit and the mixed gas outlet are sequentially connected with one another. The pressure compensation unit is provided within the reservoir and has a heat conductor which is directly contacted with the anesthetic agent to transfer heat. The vent slot is formed in the heat conductor.

Said first gas branch circuit is provided with a temperature compensation unit which adjusts the flow of the fresh gas of the first gas branch circuit according to the temperature of the vaporizing chamber. Said first gas branch circuit is further provided with a first intake valve port which is provided between the temperature compensation unit and the mixed gas outlet.

Said third pneumatic circuit is provided with a second intake valve port, and at least one of the first and the second intake valve ports has an adjustable vent aperture.

Said first and second intake valve ports are provided on the same concentration control unit which further has an outtake valve port communicating with the mixed gas outlet.

Said reservoir of the vaporizing chamber is connected with the filling unit for injecting anesthetic agent. Said first pneumatic circuit is provided with a fresh gas cut-off valve controlling the connection and disconnection of the pneumatic circuit. Said pressure compensation valve is provided in the bottom of the reservoir of the vaporizing chamber. Said heat conductor is metal.

Said pressure compensation unit further comprises a sealing washer and a cover plate. The heat conductor has a sealing surface in which the vent slot is formed. The cover plate and the heat conductor are fixed and the sealing washer is closely compressed and sealed against the sealing surface.

Said sealing surface of the heat conductor is further formed with a center hole isolated from the vent slot. Both the sealing washer and the cover plate are provided with a through hole corresponding to the center hole.

DETAILED DESCRIPTION OF THE INVENTION

Figure 1:
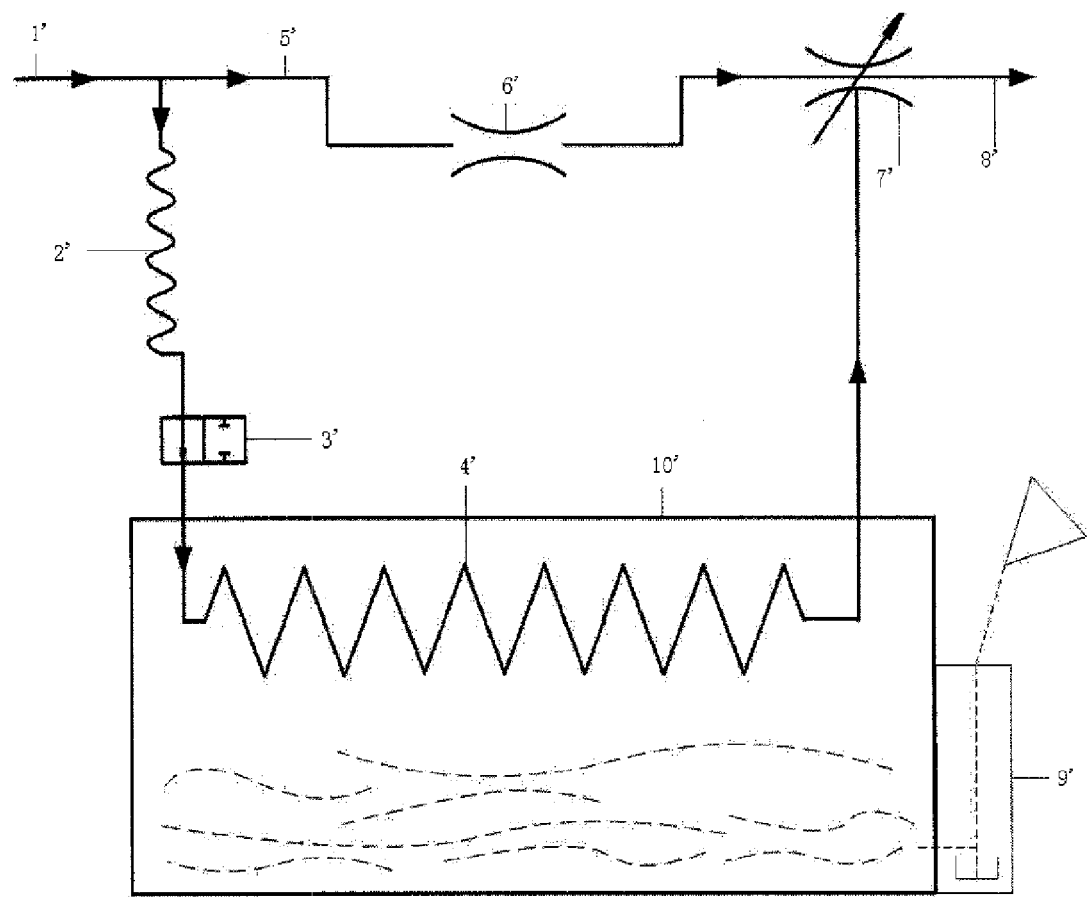
FIG. 1 is a structural principle view of a conventional anesthetic vaporizer.
Figure 2:
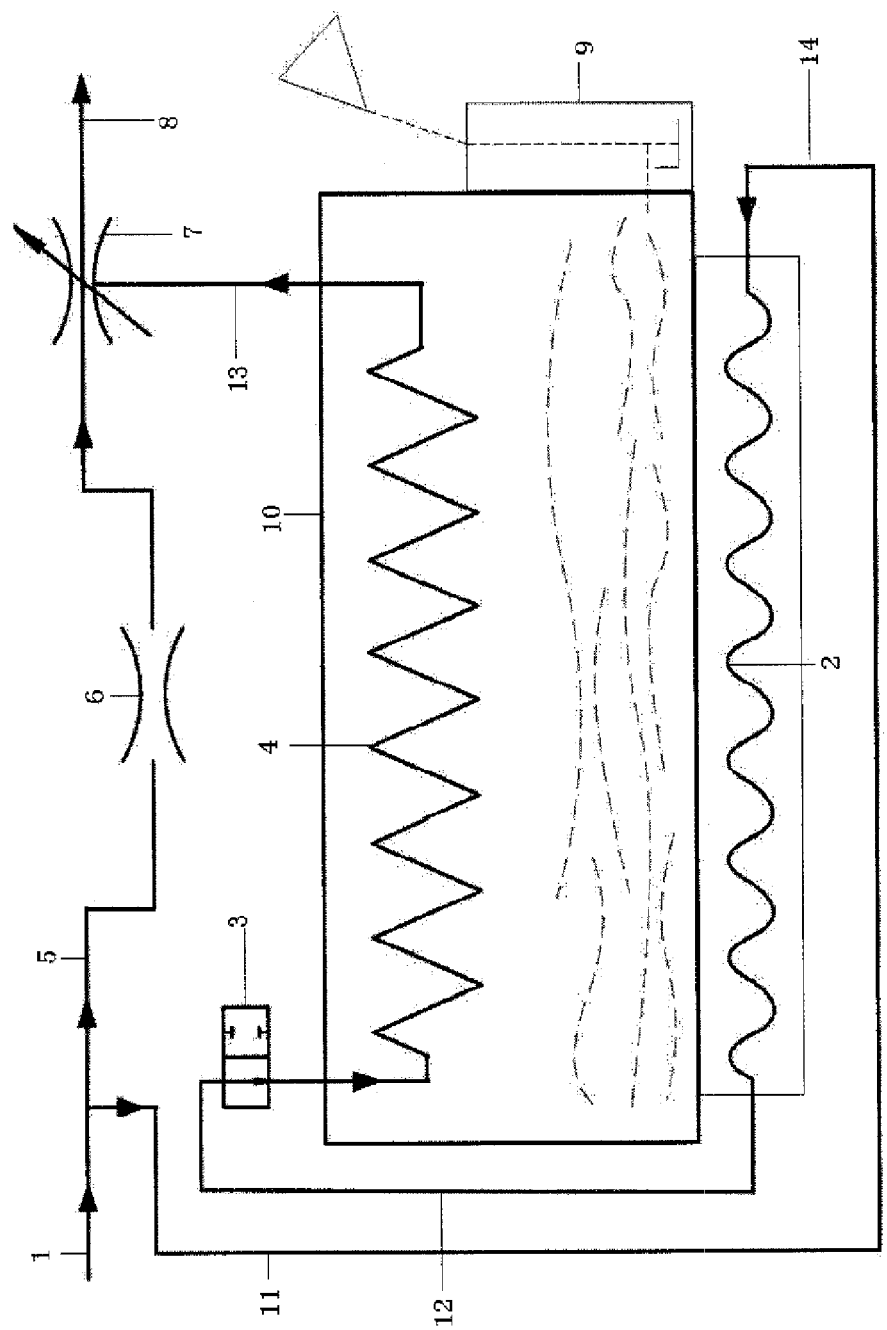
FIG. 2 is a structural principle view of an anesthetic vaporizer according to an embodiment of the present invention.

As illustrated in FIGS. 2-5, an anesthetic vaporizer according to an embodiment of the present invention comprises a fresh gas inlet 1, a mixed gas outlet 8, a vaporizing chamber 10, a filling unit 9, a first gas branch circuit 5 and a second gas branch circuit 14. The fresh gas inlet 1 is used to receive fresh gas. The mixed gas outlet 8 is used to output the mixed gases of fresh gas and anesthetic vapor. The vaporizing chamber 10 may be made of metal having good heat conductance and has a reservoir for storing anesthetic agent. The filling unit 9 is used to injecting anesthetic agent into the reservoir of the vaporizing chamber and communicated with the reservoir through a passage.

The first gas branch circuit 5 is provided with a temperature compensation unit 6 and a concentration control unit 7. The temperature compensation unit 6, which may be implemented as a valve body that can change the vent aperture of the first gas branch circuit 5, adjusts the vent aperture of the first gas branch circuit 5 according to the temperature change of the reservoir of the vaporizing chamber 10 and thus adjusts the flow of the fresh gas in the first gas branch circuit 5 so that the concentration of the anesthetic vapor in the mixed gas outputted from the mixed gas outlet 8 will not change or change slightly. If the temperature of the reservoir of the vaporizing chamber 10 rises or drops, the gas flow of the first gas branch circuit 5 is accordingly increased or decreased. The temperature compensation unit 6 may be implemented using any suitable or conventional approach, such as one having an unmovable valve port fixed on a metal pod of low expansion coefficient and a movable valve port fixed on a metal pod 19 of high expansion coefficient. When the temperature of the vaporizing chamber 10 changes, the movable valve port moves with respect to the unmovable valve port so as to change the gap between the movable valve port and the unmovable valve port. The change of the gap performs the change of the fresh gas flow in the first gas branch circuit.

The concentration control unit 7 has a first intake valve port, a second intake valve port and an outtake valve port. The vent aperture of at least one of the first intake valve port and the second intake valve port is adjustable. The outtake valve port is communicated with the mixed gas outlet. The concentration control unit 7 may be a conventional one comprising a relatively unmovable inner cone-shaped valve body and a relatively movable outer cone-shaped valve body. The concentration control unit 7 is connected with an index dial. When being rotated, the index dial takes the movable outer cone-shaped valve body to move with respect to the unmovable inner cone-shaped valve body so as to change the vent aperture of the first and the second intake valve ports and thus perform a controlled output of a desired concentration.

Figure 3:
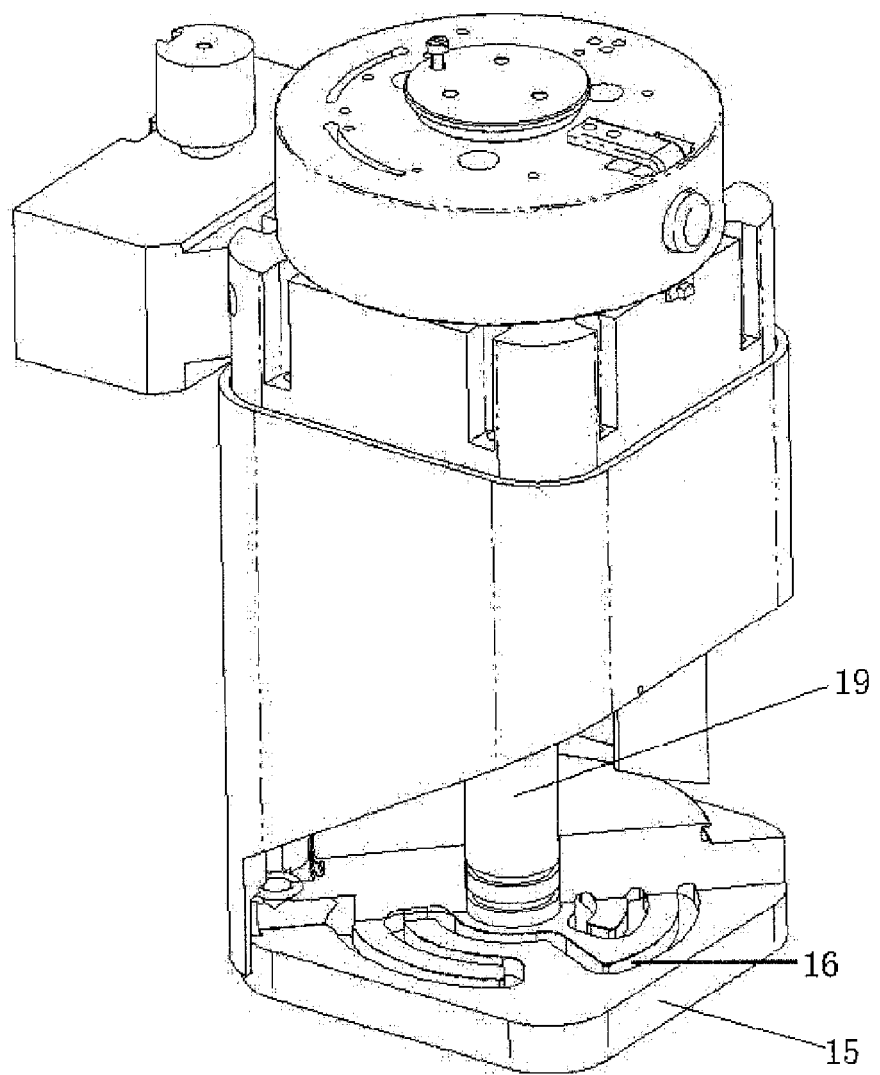
FIG. 3 is a structural schematic view of an anesthetic vaporizer according to an embodiment of the present invention.
Figure 4:
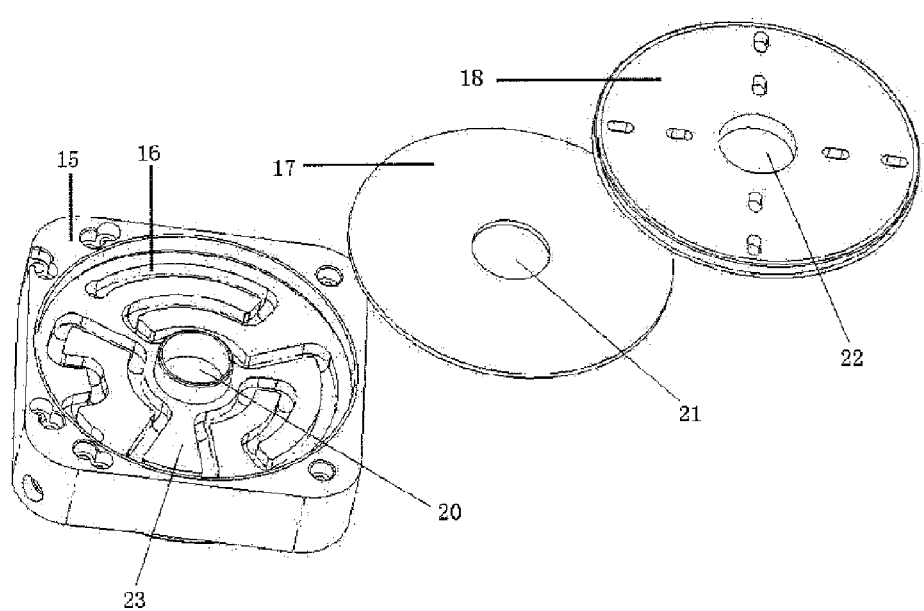
FIG. 4 is a perspective exploded view of the pressure compensation unit of an anesthetic vaporizer according to an embodiment of the present invention.
Figure 5:
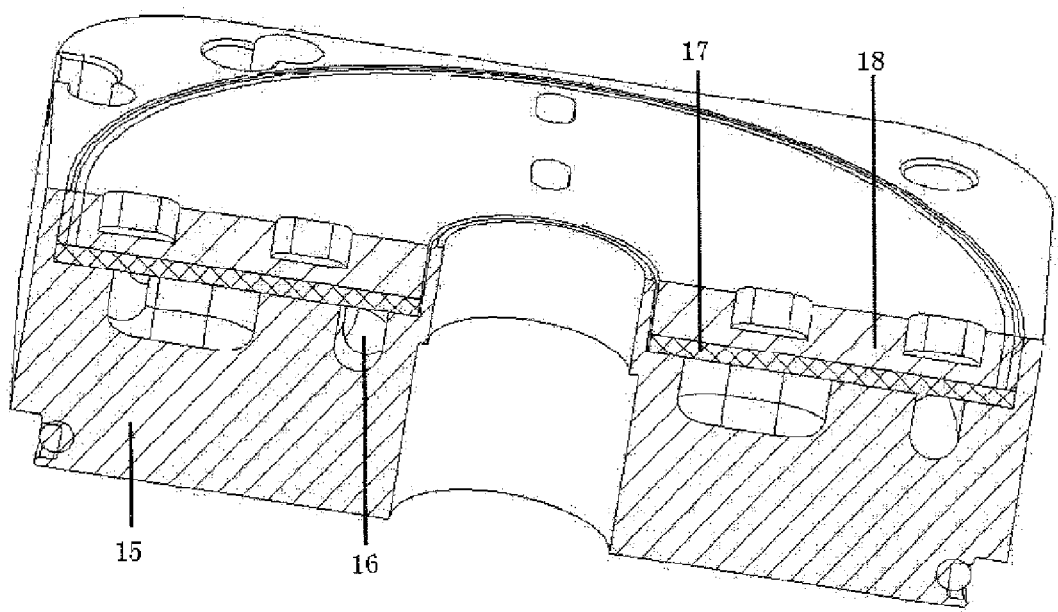
FIG. 5 is a sectional view of the pressure compensation unit of an anesthetic vaporizer according to an embodiment of the present invention.

The second gas branch circuit 14 comprises a first pneumatic circuit 11, a pressure compensation unit 2, a second pneumatic circuit 12, a wick unit 4 and a third pneumatic circuit 13. As illustrated in FIGS. 3-5, the pressure compensation unit 2 comprises a heat conductor 15, a sealing washer 17 and a cover plate 18. The heat conductor 15 is made of material of good heat conductivity such as metal. The heat conductor 15 has a sealing surface 23 which is formed to have a curved continuous vent slot 16. The cover plate 18 covers and is fixed on the heat conductor 15, and brings the sealing washer 17 to be closely compressed and sealed against the sealing surface 23 to make the vent slot 16 hermetic with respect to the surroundings. The fresh gas inlet 1, the first pneumatic circuit 11, the vent slot 16, the second pneumatic circuit 12, the wick unit 4, the third pneumatic circuit 13, the concentration control unit 7 and the mixed gas outlet 8 are sequentially connected with one another. The pressure compensation unit 2 as whole is provided in the bottom of the reservoir of the vaporizing chamber 10, and the heat conductor 15 is directly contacted with the anesthetic agent in the reservoir to transfer heat between the heat conductor 15 and the anesthetic agent. Additionally, the sealing surface 23 of the heat conductor 15 may be formed with a center hole 20 isolated from the vent slot 16. The sealing washer 17 is provided with a first through hole 21 corresponding to the center hole 20. The cover plate 18 is provided with a second through hole 22 corresponding to the center hole 20. The metal pod 19 of high expansion coefficient of the temperature compensation unit is inserted into the center hole 20 after sequentially passing through the second and the first through holes 22 and 21. The first intake valve port is provided on the first gas branch circuit 5, and the second intake valve port is provided on the third pneumatic circuit 13.

The second pneumatic circuit 12 is provided with a fresh gas control valve 3 for controlling the connection and disconnection of the pneumatic circuit. The fresh gas control valve 3 may adopt any suitable or conventional structure, for example, consisting of two relatively hermetic valve plates in which one valve plate may move with respect to the other one. Controlling of the connection and disconnection of the second pneumatic circuit 12 is achieved by the relative movement of the two valve plates.

The wick unit 4 at least partially extends into the reservoir of the vaporizing chamber 10. The extended portion can be immersed into the anesthetic agent in the reservoir so that the liquid anesthetic agent can spread over the wick unit 4. The wick unit 4 can promote the anesthetic agent in the reservoir being vaporized into gas from liquid. The larger the surface area thereof is, the better the vaporization effect is.

When the vaporizer is on the switch-off position, the fresh gas control valve 3 is on the close position. Fresh gas enters the vaporizer through the fresh gas inlet 1, passes through the first gas branch circuit 5, then arrives at the concentration control unit 7 through the temperature compensation unit 6, and flows out of the vaporizer from the mixed gas outlet 8. Since the fresh gas control valve 3 is on the switch-off position, no fresh gas enters in the vaporizing chamber 10, thus there is no anesthesia vapor being mixed in the fresh gas.

When the vaporizer is on the switch-on and above position, the fresh gas control valve 3 is on the open position. After the fresh gas enters the vaporizer through the fresh gas inlet 1, a part of the gas flows towards the pressure compensation unit 2 through the first pneumatic circuit 11, flows towards the fresh gas control valve 3 through the second pneumatic circuit 12 after passing through the vent slot 16 of the pressure compensation unit 2, and then enters the wick unit 4. Since a part of the wick unit 4 is immersed into the anesthetic agent in the vaporizing chamber 10, the wick unit 4 is filled with the saturated vapor of anesthetic gas. When flowing through the wick unit 4, the fresh gas will be mixed with part of the anesthetic vapor. The fresh gas carrying the anesthetic vapor flows through the wick unit 4, then enters the concentration control unit 7 through the third pneumatic circuit 13. The other part of the fresh gas enters the first gas branch circuit 5, and after passing through the temperature compensation unit 6, enters the concentration control unit 7 and meets the fresh gas carrying the anesthesia vapor in the concentration unit 7. By the controlling of the concentration control unit 7, the two streams of gases (the fresh gas and the fresh gas carrying anesthetic vapor) are mixed at a certain ratio and outputted out of the vaporizer from the mixed gas outlet 8.

The anesthetic vaporizer according to some embodiments of the invention comprises a fresh gas inlet, a mixed gas outlet, a first gas branch circuit, a second gas branch circuit and a vaporizing chamber. The vaporizing chamber has a reservoir for containing anesthetic agent. The first gas branch circuit connects the fresh gas inlet and the mixed gas outlet. The second gas branch circuit comprises a first pneumatic circuit, a pressure compensation unit, a second pneumatic circuit, a wick unit and a third pneumatic circuit. The pressure compensation unit has a curved continuous sealed vent slot. The wick unit has an immersion portion which is directly contacted with the anesthetic agent in the reservoir. The fresh gas inlet, the first pneumatic circuit, the vent slot, the second pneumatic circuit, the wick unit, the third pneumatic circuit and the mixed gas outlet are sequentially connected with one another.

The pressure compensation unit is provided in the reservoir and has a heat conductor which is directly contacted with the anesthetic agent to transfer heat. The vent slot is formed in the heat conductor. The pressure compensation unit can prevent reverse flow due to pressure change at the mixed gas outlet and alleviate the adverse influence of the pressure change at the fresh gas inlet on the whole anesthetic vaporizer, since the pressure compensation unit is designed with a curved vent slot. The pressure compensation unit is provided in the reservoir of the vaporizing chamber, and the heat conductor is contacted directly with the anesthetic agent. During the use of the anesthetic vaporizer, the anesthetic vaporizes and absorbs heat. The temperature of the heat conductor of the pressure compensation unit approximates to that of the anesthetic agent but is lower than that of the fresh gas flowed through the fresh gas inlet. When the fresh gas flows continuously through the pressure compensation unit, the fresh gas transfers heat to the heat conductor and the heat conductor in turn transfers heat to the anesthetic agent, serving as restraining the temperature drop of the anesthetic agent, thereby slowing down the dropping speed of the temperature of the anesthetic agent, and directly providing an effective help to stabilize the concentration of the anesthetic vapor in the mixed gas outputted from the whole anesthetic vaporizer, whereby the actual value of the concentration of the anesthetic vapor in the outputted gas approximates to the set concentration value more closely.

In the anesthetic vaporizer according to some embodiments of the invention, the pressure compensation unit is preferably an independent unit as whole so as to facilitate processing and assembly and is easier to be accomplished. The pressure compensation unit may be placed in the bottom of the reservoir of the vaporizing chamber so as to effectively save the space of the whole anesthetic vaporizer and make the structure of the whole anesthetic vaporizer more compact. Of course, the pressure compensation unit may be alternatively positioned in the side portion or other portions of the reservoir as long as the heat conductor can directly contact the anesthetic agent. The pressure compensation unit has a vent slot which is hermetic with respect to the surroundings. The hermetic vent slot may be embodied by the fixedly integrated heat conductor, sealing washer and cover plate. A hole may or may not be formed in the center of the heat conductor, the sealing washer and the cover plate of the pressure compensation unit.

In the anesthetic vaporizer according to some embodiments of the invention, the first gas branch circuit may be provided with a temperature compensation unit for adjusting the gas flow of the gas branch circuit according to the temperature of the vaporizing chamber. By the cooperating use of the temperature compensation unit and the pressure compensation unit, the concentration of the anesthetic vapor outputted from the vaporizer approximates to the set one more closely. The first gas branch circuit may be further provided with a first intake valve port positioned between the temperature compensation unit and the mixed gas outlet. The third gas branch circuit may be further provided with a second intake valve port. The vent aperture of at least one of the first intake valve port and the second intake valve port may be adjustable so as to perform the adjusting of the flow of the fresh gas entered in the concentration control unit and/or the flow of the fresh gas carrying anesthetic vapor, and thus the adjusting of the concentration of the anesthetic vapor outputted from the vaporizer. The first intake valve port and the second inlet valve may be provided in members independent to each other, and alternatively may be both provided in the same concentration control unit having a first and a second intake valve ports and an outtake valve port. Alternatively, of course, both the first pneumatic circuit and the second pneumatic circuit are not provided with adjustable valve ports controlling gas flow.

In the anesthetic vaporizer according to the invention, the reservoir of the vaporizing chamber may be communicated with the filling unit for injecting anesthetic agent. The heat conductor of the pressure compensation unit may be metal, and alternatively may be made of other materials of good heat conductance. The vaporizing chamber may be made of metal and alternatively of other materials of good heat conductance.

The above describes the invention in detail in conjunction with specific preferred embodiments, but the invention should not be considered to be limited to the embodiments. It will be apparent to those skilled in the art that various modifications and changes may be made without departing from the essence of the invention and should be considered to fall into the scope of the invention.

What is claimed is:

1. An anesthetic vaporizer, comprising:
    a fresh gas inlet;
    a mixed gas outlet;
    a first gas branch circuit;
    a second gas branch circuit and a vaporizing chamber,
        the vaporizing chamber having a reservoir for containing an anesthetic agent,
        the first gas branch circuit connecting the fresh gas inlet and the mixed gas outlet, and
        the second gas branch circuit comprising a first pneumatic circuit,
    a pressure compensation unit;
    a second pneumatic circuit; and
    a wick unit and a third pneumatic circuit;
        the pressure compensation unit having a curved, continuous, and sealed vent slot,
        the wick unit having an immersion portion which directly contacts the anesthetic agent in the reservoir,
        the fresh gas inlet, the first pneumatic circuit, the sealed vent slot, the second pneumatic circuit, the wick unit, the third pneumatic circuit, and the mixed gas outlet being sequentially connected with one another, characterized in that
        the pressure compensation unit is provided in or near the reservoir and has a heat conductor which is to contact the anesthetic agent to transfer heat, and
        the sealed vent slot is formed in the heat conductor.

2. The anesthetic vaporizer as in claim 1, characterized in that said first gas branch circuit is provided with a temperature compensation unit which adjusts a flow of fresh gas of the first gas branch circuit according to temperature of the vaporizing chamber.

3. The anesthetic vaporizer as in claim 2, characterized in that said first gas branch circuit is further provided with a first intake valve port which is provided between the temperature compensation unit and the mixed gas outlet.

4. The anesthetic vaporizer as in claim 3, characterized in that said third pneumatic circuit is provided with a second intake valve port, and at least one of the first intake valve port and the second intake valve ports has an adjustable vent aperture.

5. The anesthetic vaporizer as in claim 4, characterized in that said first intake valve port and the second intake valve port are provided on same concentration control unit which further has an outtake valve port communicating with the mixed gas outlet.

6. The anesthetic vaporizer as in claim 1, characterized in that said reservoir of the vaporizing chamber is connected with a filling unit that is to inject the anesthetic agent.

7. The anesthetic vaporizer as in claim 1, characterized in that said first pneumatic circuit is provided with a fresh gas cut-off valve controlling connection and disconnection of the first pneumatic circuit.

8. The anesthetic vaporizer as in claim 1, characterized in that said pressure compensation unit is provided at a bottom of the reservoir of the vaporizing chamber.

9. The anesthetic vaporizer as in claim 1, characterized in that said heat conductor comprises a metal element.

10. The anesthetic vaporizer as in any of claims 1-9, characterized in that said pressure compensation unit further comprises a sealing washer and a cover plate, the heat conductor having a sealing surface in which the sealed vent slot is formed, the cover plate and the heat conductor being fixed, and the sealing washer being compressed and sealed against the sealing surface.

11. The anesthetic vaporizer as in claim 10, characterized in that said sealing surface of the heat conductor is further formed with a center hole isolated from the vent slot, both the sealing washer and the cover plate being provided with a respective through hole corresponding to the center hole.

12. An anesthetic vaporizer, comprising:
    a fresh gas inlet to receive fresh gas to be mixed with an anesthetic agent;
    a mixed gas outlet;
    a vaporizing chamber, the vaporizing chamber having a reservoir to contain the anesthetic agent; and
    a pressure compensation unit to control pressure based at least in part upon pressure levels at the fresh gas inlet or the mixed gas outlet, wherein
        the pressure compensation unit includes a heat conductor which transfers heat to the anesthetic agent, and
        the heat conductor includes a sealing surface on which a vent slot for at least a portion of the fresh gas to flow through before the at least the portion of the fresh gas is mixed with the anesthetic agent is formed.

13. The anesthetic vaporizer of claim 12, in which the heat is transferred from fresh gas to the anesthetic agent.

14. The anesthetic vaporizer of claim 12, in which the pressure compensation unit is provided at a bottom of the reservoir of the vaporizing chamber.

15. The anesthetic vaporizer of claim 12, in which the heat conductor comprises a metal element to transfer heat.

16. The anesthetic vaporizer of claim 12, in which the pressure compensation unit comprises a sealing washer and a cover plate, the heat conductor having the sealing surface on which the vent slot is formed, and the cover plate and the heat conductor being fixed and the sealing washer being compressed and sealed against the sealing surface.

17. The pressure compensation unit for the anesthetic vaporizer of claim 12, comprising:
    an opening to conduct the fresh gas from the fresh gas inlet of the anesthetic vaporizer; and
    the heat conductor which transfers the heat to the anesthetic agent that is contained within the reservoir of the vaporizing chamber, wherein
        the heat conductor comprises a thermally conductive material to transfer the heat from the fresh gas to the anesthetic agent.

18. The pressure compensation unit of claim 17, in which the heat conductor comprises a metal element.

19. The pressure compensation unit of claim 17, in which the pressure compensation unit further comprises a sealing washer and a cover plate, the heat conductor having a sealing surface on which a vent slot is formed, the cover plate and the heat conductor being fixed, and the sealing washer being compressed and sealed against the sealing surface.

20. The anesthetic vaporizer of claim 12, in which the at least a portion of the fresh gas is allowed to flow through the vent slot on the sealing surface before the at least the portion of the fresh gas is mixed with the anesthetic agent.

* * * * *